United States Patent [19]

Kallenbach et al.

[11] Patent Number: 5,756,323
[45] Date of Patent: May 26, 1998

[54] METHOD FOR GENERATING STRUCTURAL AND FUNCTIONAL DIVERSITY IN A PEPTIDE SEQUENCE

[75] Inventors: Sacha Kallenbach, Nanterre; Noelle Doyen, Paris; Francois Rougeon, Poigny La Foret, all of France

[73] Assignee: Institut Pasteur, Paris Cedex, France

[21] Appl. No.: 244,378

[22] PCT Filed: Dec. 11, 1992

[86] PCT No.: PCT/FR92/01178

§ 371 Date: Sep. 1, 1994

§ 102(e) Date: Sep. 1, 1994

[87] PCT Pub. No.: WO93/12228

PCT Pub. Date: Jun. 24, 1993

[30] Foreign Application Priority Data

Dec. 11, 1991 [FR] France .................. 91/15389

[51] Int. Cl.⁶ .......................... C12N 15/01; C12N 15/12
[52] U.S. Cl. ............................... 435/172.3; 536/23.2
[58] Field of Search .................... 435/172.3; 536/23.2

[56] References Cited

PUBLICATIONS

Watson et al. Molecular Biology of the Gene, Fourth Edition pp. 313–338 Benjamin Cummings Pub. Co. (1987).
Kallenbach et al. Proc. Natl. Acad. Sci. USA 89 2799–2803 (1992) Three Lymphoid Specific Factors Account for all ...
Oettinger et al. Science 248 1517–1523 (1990).
Rag-1 and Rag-2, Adjacent Genes that Synergistically ...
Kallenbach et al. Nucleic Acids Research 18 6730 (1990) A Rapid Test for U(O)J Recombinase Activity.
Kowai et al. Nucleic Acids Research 14 5777–5792 (1986) Isolation and Characterization of Bovine and Mouse Terminal ...
Landau et al. Molecular and Cellular Biology 7 3237–3243 (1987) Increased Frequency of N-region Insertion in a Murine Pre–B–cell ....
Huse et al. Science 246 1275–1281 (1989) Generation of a Large Combinatorial Library of the Immunoglobulin ....
Davis Annual Review of Biochemistry 59 475–496 (1990) T Cell Receptor Gene Diversity and Selection.
Hasty et al. Human neutrophil collagenase J. Biol. Chem. vol. 265 11421–11424, 1990.

*Primary Examiner*—James Ketter
*Assistant Examiner*—John S. Brusca
*Attorney, Agent, or Firm*—Oblon, Spivak, McClelland, Maier & Neustadt, P.C.

[57] ABSTRACT

The invention relates to a method for generating structural and functional diversity in a peptide sequence by randomly deleting and inserting nucleotides in a nucleotide sequence which codes for the peptide sequence. This method may be carried out by transfecting a cell preparation with vectors allowing expression of the Rag-1 and Rag-2 genes and optionally the terminal deoxynucleotidyl transferase gene, as well as with a vector including the nucleotide sequence which codes for the peptide sequence.

20 Claims, 3 Drawing Sheets

```
CCGCTCTAGAACTAGTGGATCC-CACAGTG- (12)
                       (23) -CACTGTG-GTCGACCTCGAGGGG
```

| | | |
|---|---|---|
| CCGCTCTAGAACTAGTGGAT-- | | ----ACCTCGAGGGG |
| CCGCTCTAGAACTAGTGGATCC | | GTCGACCTCGAGGGG |
| CCGCTCTAGAACTAGTGGATCC | | GTCGACCTCGAGGGG |
| CCGCTCTAGAACTAGTGGATCC | | GTCGACCTCGAGGGG |
| CCGCTCTAGAACTAGTGGATCC | | GTCGACCTCGAGGGG |
| CCGCTCTAGAACTAGTGGATCC | | ---GACCTCGAGGGG |
| CCGCTCTAGAACTAGTGGATCC | | GTCGACCTCGAGGGG |
| CCGCTCTAGAACTAGTGGATCC | | ---GACCTCGAGGGG |
| CCGCTCTAGAACTAGTGG---- | | --CGACCTCGAGGGG |
| CCGCTCTAGAACTAGTGGATCC | | ---GACCTCGAGGGG |
| CCGCTCTAGAACTAGTG----- | | -------TCGAGGGG |
| CCGCTCTAGAACTAGTGGATCC | | GTCGACCTCGAGGGG |
| CCGCTCTAGAACTAGTGGATCC | | ---GACCTCGAGGGG |
| CCGCTCTAGAACTAGTGGATCC | | GTCGACCTCGAGGGG |
| CCGCTCTAGAACTAGTGGATCC | GG | --CGACCTCGAGGGG |
| CCGCTCTAGAACTAGTGG---- | | --CGACCTCGAGGGG |
| CCGCTCTAGAACTAGTGGATCC | C | -TCGACCTCGAGGGG |

*FIG. 1*

```
CCGCTCTAGAACTAGTGGATCC-CACAGTG- (12)
                       (23) -CACTGTG-GTCGACCTCGAGGGG

CCGCTCTAGAACTAGTGG----      GTTC              GTCGACCTCGAGGGG
CCGCTCTAGAACTAGTGGATCC      GG                -----CCTCGAGGGG
CCGCTCTAGAACTAGTGG----      GGCC              GTCGACCTCGAGGGG
CCGCTC----------------      TTTC              GTCGACCTCGAGGGG
CCGCTCTAGAACTAGT------      TT                -----CCTCGAGGGG
CCGCTCTAGAACTAGTGG----      G                 GTCGACCTCGAGGGG
CCGCTCTAGAACTAGTGGATCC      CCA               ---GACCTCGAGGGG
CCGCTCTAGAACT---------      T                 -TCGACCTCGAGGGG
CCGCTCTAGAACTAGTGGATCC      GAC               GTCGACCTCGAGGGG
CCGCTCTAGAACTAGTGGATCC      ATC               --CGACCTCGAGGGG
CCGCTCTAGAACTAGTGGATCC      A                 ----ACCTCGAGGGG
CCGCTCTAGAACTAGTG-----                        ----ACCTCGAGGGG
CCGCTCTAGAACTAGTGGATCC      TCC               GTCGACCTCGAGGGG
CCGCTCTAGAACTAGTGGATCC                        GTCGACCTCGAGGGG
CCGCTCTAGAACTAGTGGATCC      CTC               GTCGACCTCGAGGGG
CCGCTCTAGAACTAGTGG----      GTCC              GTCGACCTCGAGGGG
CCGCTCTAGAACTAGTGGATC-      GGG               -----CCTCGAGGGG
CCGCTCTAGAACTAGTGGATCC      GAG               GTCGACCTCGAGGGG
CCGCTCTAGAACTAGTGGATC-      G                 ---GACCTCGAGGGG
CCGCTCTAGAACTAGTGGATCC                        GTCGACCTCGAGGGG
CCGCTCTAGAACTAGTGGAT--      ACCATACCCCTTTACCAA -TCGACCTCGAGGGG
CCGCTCTAGAACTAGTGGATCC      CCCCCCGCC         GTCGACCTCGAGGGG
CCGCTCTAGAACTAGTGG----      TCCT              -----CCTCGAGGGG
CCGCTCTAGAACTAGTGGATC-      AC                ----ACCTCGAGGGG
CCGCTCTAGAACTAGTGG----      CC                ---GACCTCGAGGGG
CCGCTCTAGAACTAG-------      CCCTAC            --CGACCTCGAGGGG
CCGCTCTAGAACTAGTGG----      CCC               --CGACCTCGAGGGG
CCGCTCTAGAACTAGTGGATCC                        GTCGACCTCGAGGGG
CCGCTCTAGAACTAGTGG----      TCC               --CGACCTCGAGGGG
CCGCTCTAGAACTAGTGGAT--      TC                GTCGACCTCGAGGGG
CCGCTCTAGAACTAGTGG----      TC                -TCGACCTCGAGGGG
CCGCTCTAGAACTAGTGGATCC      A                 ----ACCTCGAGGGG
CCGCTCTAGAACTAGTGGATCC      CCC               GTCGACCTCGAGGGG
```

*FIG. 2*

```
CCGCTCTAGAACTAGTGGATCC-CACAGTG- (12)
                       (23) -CACTGTG-GTCGACCTCGAGGGG
```

BW1 J
```
CCGCTCTAGAACTAGTGG----                    ---GACCTCGAGGGG
CCGCTCTAGAACTAGTGG----                    ----ACCTCGAGGGG
CCGCTCTAGAACTAGTGGATCC                    GTCGACCTCGAGGGG
CCGCTCTAGAACTAGTGGATCC                    ---GACCTCGAGGGG
```

CHO-K1
```
CCGCTCTAGAACTAGTGGATCC                    ---GACCTCGAGGGG
CCGCTCTAGAACTAGTGGATCC                    GTCGACCTCGAGGGG
```

A9
```
CCGCTCTAGAACTAGTGGATCC        GG          -----CCTCGAGGGG
CCGCTCTAGAACTAGTGGATCC                    GTCGACCTCGAGGGG
CCGC------------------                    ---GACCTCGAGGGG
CCGC------------------                    GTCGACCTCGAGGGG
CCGCTCTAGAACTAGTGGATC-                    ---GACCTCGAGGGG
```

*FIG. 3*

METHOD FOR GENERATING STRUCTURAL AND FUNCTIONAL DIVERSITY IN A PEPTIDE SEQUENCE

The present invention relates to a method for generating structural or functional diversity in a peptide sequence by introducing insertions or deletions of nucleotides in the nucleotide sequence which codes for the said peptide sequence.

The present invention also relates to pharmaceutical compositions, drugs or diagnostic reagents containing proteins or peptides obtained by this method.

The mature genes coding for the constituent chains of immunoglobulins and T cell receptors are assembled early during lymphocyte development from gene segments termed variability (V), linking, or junction (J), and in some cases diversity (D).

Seven loci are able to be rearranged by recombination of these fragments.

The recombination signal sequences (RSS) adjacent to each gene supply the targets for the recombination. These sequences are composed of a palindromic heptamer and a nonamer rich in adenosine and thymidine, separated by a sequence of 12 or 23 base pairs. The rearrangements are made between RSS with separation sequences of different lengths.

Two types of junction or linking are formed during the recombination: coding junctions created by the juxtaposition of gene segments and noncoding junctions formed by contiguous RSS. In the latter case, the heptamers are generally joined without nucleotide insertions or deletions. The coding junctions themselves are liable to substantial modifications.

The variations in the junctions during the rearrangement of the gene segments coding for the immunoglobulins represent a major source of diversity. Several nucleotides can thus be eliminated and two types of insertion can occur.

The random addition of nucleotides results in the insertion of regions termed N regions in the immunoglobulin heavy chains. The hypothesis has been advanced (Randau et al., Molecular and Cellular Biology, 1987, 3237–3243) that the deoxynucleotidyl transferase (TdT) is responsible for this random addition of nucleotides.

The type P nucleotides insertions correspond to the inverse repetition of sequences adjacent to those of the coding sequences. The hypothesis has been advanced that their addition represents a necessary step in the recombination mechanism.

Transfection experiments with genomic DNA have enabled the isolation of two genes actively involved in the recombination: the Rag-1 and Rag-2 genes (Oettinger et al., Science, Volume 248, 1517–1523, 1990).

It has been shown that the Rag-1 and Rag-2 genes are responsible for the site-specific recombination.

Nevertheless, the combination of the products of the Rag-1 and Rag-2 genes does not restore the diversity of antibodies found in vivo, in other words does not allow to add the N sequences.

Various methods have been developed to attempt to modify the immunoglobulin heavy and light chains or the receptors.

EP patent No-368.684 relates to a method for cloning nucleotide sequences corresponding to the variable regions of the molecules in the immunoglobulin family. This method consists of producing a DNA complementary to the variable region of the immunoglobulin.

EP patent No-328.444 relates to a method for modifying the structure of an antibody while retaining its functional specificity. Thus, the constant regions in particular are modified by a classical genetic engineering technique.

To the knowledge of the applicant, there is no method for efficiently obtaining structurally modified immunoglobulins with a wide diversity in the modifications.

The applicant has thus aimed to demonstrate recombination mechanisms which allow the organism to achieve a wide diversity in the immunoglobulins such as the IgG, the IgM, the IgA, the IgE, and in the lymphoid cell receptors.

The applicant has also aimed to develop a general method for randomly obtaining a very diversified range of mutations, in particular by random insertion, in the nucleotide sequence corresponding to proteins with various structures and functions.

The applicant has also found that the combination of the products of expression of the Rag-1 and Rag-2 genes leads unexpectedly to a site-specific recombination and that the introduction of the TdT leads to a junction diversity between the DJ and VDJ sequences equivalent to those found in vivo.

The applicant has also shown that it is possible, by use of the Rag-1 and Rag-2 products as well as the terminal deoxynucleotidyl transferase, to obtain in vitro the production of antibodies showing rearrangements, and which statistically show an extensive structural and functional diversity.

The present invention thus relates to a composition containing a combination of synergistic quantities of the products of expression of the Rag-1 and Rag-2 genes and a terminal deoxynucleotidyl transferase or one or more of their biologically active fragments.

It also relates to a composition containing the nucleotide sequences including the Rag-1 and Rag-2 genes or the genes leading to the synthesis of fragments or biologically active derivatives of the products of the Rag-1 and Rag-2 genes and the gene coding for the TdT or one of its fragments or biologically active derivatives, in which the nucleotide sequences are advantageously carried by vectors.

It in addition relates to a composition comprising the plasmids p Blue Rec (Kallenbach et al., Nucleic Acid Research, 18, 6730, 1990), p Rag-1 and p Rag-2 (Oettinger et al, previously referred to).

The present invention also relates to

- a method for generating structural or functional diversity in a peptide sequence by randomly deleting or inserting nucleotides in a nucleotide sequence which codes for this peptide sequence, the said method comprising the transfection of a cell preparation with one or more vectors allowing expression of the products of the Rag-1, Rag-2 genes and the terminal deoxynucleotidyl transferase (TdT) or of their derivatives and by an identical or different vector including the said nucleotide sequence bordered by one or more RSS recombination sequences or bordered by one or more biologically active derivatives of the RSS sequences.

- a method for generating structural or functional diversity in a peptide sequence by randomly deleting or inserting nucleotides in a nucleotide sequence which codes for this peptide sequence, the said method comprising the transfection of a cell preparation with a vector including the said nucleotide sequence bordered by one or more RSS recombination sequences or bordered by one or more biologically active derivatives of the RSS sequences, then in a second step by one or more identical or different vectors allowing expression of the products of the Rag-1, Rag-2 genes and terminal deoxynucleotidyl transferase or of their derivatives.

- a method for generating structural or functional diversity in a peptide sequence by introducing into the nucleotide sequence corresponding to this peptide sequence insertions or deletions resulting from the inverse repetition of sequences adjacent to the RSS recombination sequences, the said method comprising the transfection of a cell preparation with one or more vectors allowing expression of the products of the Rag-1 and Rag-2 genes or of their derivatives and by an identical or different vector including the said nucleotide sequence bordered by one or more RSS sequences or by one or more biologically active derivatives of the RSS sequences.

a method for generating structural or functional diversity in a peptide sequence by introducing into the nucleotide sequence corresponding to this peptide sequence insertions or deletions resulting from the inverse repetition of sequences adjacent to the RSS recombination sequences, the said method comprising the transfection of a cell preparation with a vector including the said nucleotide sequence bordered by one or more RSS sequences or by one or more biologically active derivatives of the RSS sequences, then in a second step by one or more identical or different vectors allowing expression of the products of the Rag-1 and Rag-2 genes or of their derivatives.

Such methods also allow the random introduction of insertions and deletions into nucleotide sequences. These sequence modifications thus allow the biological diversity to be increased at will.

Such methods are in particular interesting substitutes for the traditional methods of mutagenesis and for methods of obtaining monoclonal antibodies by hybridomas.

The possibility of obtaining monoclonal antibodies by a method other than from hybridomas is advantageous in human therapeutics since the antibody preparations obtained according to the invention are pure.

It should be remembered that N sequences mean random insertions of nucleotides, or in other words those which are not replicas of sequences already existing in the neighborhood of the RSS.

These N sequences are thus created randomly and as a result show a very wide diversity, which is not dependent on the nucleotide sequence in the neighborhood of the RSS.

The P sequences are on the other hand insertions resulting from the inverse repetition of sequences adjacent to the RSS.

As a result, they show less diversity than the N regions.

Advantageously, the recombined vector or vectors including the nucleotide sequence corresponding to the peptide sequence are transferred into bacteria in order to select the proteins or peptides showing the structure and/or function desired.

It should be noted that it is necessary to choose expression vectors for the proteins or peptides which are suited to the cells, eukaryotes or prokaryotes, used. It is also possible to use the plasmids pcDNAI (marketed by In vitrogen) or pRc/CMV (marketed by In Vitrogen) for the eukaryotic cells or the plasmid pBlue Script (marketed by Stratagen)

The present invention also relates to a preferential use of the method for obtaining immunoglobulins, in particular antibodies showing a wide structural and functional diversity by separate rearrangements of the light and heavy chains making up the immunoglobulins and co-expression of the two chains in the same cell.

Thus, this preferential mode of application allows the production of a large quantity of cells expressing varied sequences of the two immunoglobulin chains. A subsequent step allows the selection of the specific immunoglobulin for a given pathogenic agent, for example.

Advantageously, the sequence corresponding to the heavy chains used only includes the Fab. part of these chains. The Fc part is added later.

Preferentially, the rearrangement of the light chains is carried out in the presence of the nucleotide sequences of the Rag-1 and Rag-2 genes or of genes leading to the synthesis of biologically active derivatives or fragments of the products of Rag-1 and Rag-2, and the rearrangement of the heavy chains is carried out in the presence of the nucleotide sequences of the Rag-1 and Rag-2 genes and of the terminal deoxynucleotidyl transferase gene or of genes leading to the synthesis of biologically active derivatives or fragments of Rag-1, Rag-2 or the TdT.

In order to obtain the expression of the immunoglobulin heavy chains, vectors including the V, D and J segments are used, while for the light chains the vectors include the v and J sequences.

The present invention in addition relates to a method for obtaining receptors of lymphoid cells, and in particular T cells, showing a wide structural and functional diversity by rearrangement of the alpha, beta, gamma and/or delta chains of the T cell receptors.

It also relates to a method comprising the steps of:

a) transfection of a cell preparation with one or more vectors including a nucleotide sequence which codes for the peptide sequence for which the variability is desired and by one or more identical or different vectors allowing expression of the Rag-1 and Rag-2 genes or expression of the Rag-1, Rag-2 genes and the TdT;

b) isolation of the DNA of the vectors of the cell preparations;

c) removal of the vectors which have not undergone recombination;

d) transformation of the cell hosts by the vectors resulting from step c), and e) selection of the cell hosts expressing the molecules showing the structure and/or function sought for.

Advantageously, this method comprises the steps of:

a) co-transfection of a cell preparation with one or more vectors including the genes which code for the non-rearranged light chains and by one or more vectors expressing the genes which code for Rag-1 and Rag-2, their derivatives and/or their fragments, and b) co-transfection of another cell preparation by one or more vectors including the genes which code for the non-rearranged heavy chains and by one or more vectors expressing the gene for the terminal deoxynucleotidyl transferase in addition to the genes coding for Rag-1 and Rag-2, c) isolation of the vector DNA of the two cell preparations, d) removal of the vectors which have not undergone recombination, e) transformation of at least two bacterial cultures respectively by the vector preparations obtained from step d), amplification and preparation of the bacterial vector DNA, f) insertion of the genes which code for the heavy and light chains into the same vector, g) transformation of the cell hosts by the vector obtained from step f), and h) selection of the cell hosts expressing the complete immunoglobulin molecules.

Cell hosts are here taken to mean any eukaryotic bacteria or cells able to be transformed or transfected.

In the present application, vector is taken to mean any autoreplicative DNA molecule able to be transferred from one cell to another. Plasmids are preferentially used in steps a) to h) but any other vector compatible with the cell and bacterial systems used may advantageously be used.

The vectors obtained at step c) that have not undergone recombination are advantageously removed by enzymatic digestion at a site specifically recognized by a restriction endonuclease.

The cells preferentially used in steps a) and b) are fibroblasts or lymphoid cells, or any other eukaryotic cell type or cell line.

It should be noted that the vectors used preferentially contain the precocious region of the polyome in order to allow their replication at the autonomous state of the eukaryotic cells.

The selection of the bacteria at step h) is advantageously carried out by filter replication of the bacterial colonies obtained by spreading the bacteria on Petri dishes and subsequent screening ["Molecular cloning ; a Laboratory Manual" (Sambrok et al., Cold Spring Harbor Laboratory Press, New York, 1989)] with the antigens for the required specific antibodies.

It should also be noted that the vectors expressing the antibodies or the lymphoid cell receptors sought for may subsequently be modified so as to allow the expression of complete immunoglobulins in the eukaryotic cells, and in particular so as The methodir glycosylation.

The methods by which steps a) to h) may be carried out are well known to those skilled in the art. In general, "Molecular cloning; a Laboratory Manual", (Sambrok et al., Cold Spring Harbor Laboratory Press, New York, 1989) may be referred to.

Some practical applications of these steps are also described in the article by Huse et al. (Science, volume 246, 1275–1281, 1989).

In particular, the vector used in step a) may be the plasmid p Blue Script containing a cassette of the type fragment EcoRI-Not I of lambda Lcl described in this article in which are inserted a V segment and a J segment attached to the constant region of the light chain. The VL and JL segments are bordered by their recombination signal sequences.

The vector used for the co-transformation of step b) may be the plasmid p Blue Script containing a cassette of the type fragment NotI-EcoRI of lambda Hc2 described in this article in which are inserted a V segment, a D segment and a J segment attached to the CH1 region of the heavy chain. The VH, DH and JH segments are bordered by their recombination signal sequences.

The expression vectors of the Rag-1 and Rag-2 genes used in steps a) and b) may be those described by Qettinger et al. (Science, 248, 1517–1523, 1990).

The cloning vector including the gene which codes for the terminal deoxyribonucleotidyl transferase may in particular be the plasmid pMTdT which is a pcDNAII in which the complementary DNA of the mouse terminal deoxyribonucleotidyl transferase has been inserted.

The present application also relates to this plasmid, which was deposited on 10 Dec. 1991 with the Microorganism Culture National Collection of the Institut Pasteur under the n. I 1160.

The previously mentioned article by Huse et al. moreover mentions some practical applications which may be used within the scope of the present invention.

In particular, the vectors used in steps a) and b) may be obtained from a library created as described in this article.

This library may be obtained by cloning the light and heavy chain fragments in respectively the vectors generated from phage lambda, lambda Lc1 and lambda Hc2. These vectors, which carry out the cloning in the initial stage of the library creation, can be excised to give rise to a plasmid containing oligonucleotide fragments corresponding to the heavy and light chains.

These vectors contain various restriction sites, and a sequence which codes for the leader peptide of the bacterial gene PelB which has previously been successfully used in E. coli to secrete Fab fragments, a ribosome binding site, and on the lambda Hc2 vector a sequence corresponding to the tag decapeptide located at the C terminal end of the insertion into the heavy chain. The tag peptide enables the expression products to be purified by passage through immunoaffinity columns.

The DNA used as the basis for creating the heavy chain library is preferentially human DNA in order to minimize the risk of rejection by the organism in the case of the use of these antibodies in human therapeutics.

The use of step f), which is the insertion of the genes coding for the heavy and light chains into the same vector, can be carried out as described on page 1278 of the article by Huse et al. previously referred to.

The library of light chains is thus digested by the restriction endonuclease cleaving at a unique site, the resulting 5' extremities are dephosphorylated, and the products are then digested by another restriction endonuclease Eco R1 cleaving at a unique site.

The DNA of the vectors constituting the library of heavy chains is cleaved by the endonuclease Hind-III, then dephosphorylated and digested by endonuclease Eco R1.

The DNA thus prepared are mixed and linked by ligation.

After ligation, only the clones which result from the combination of a fragment derived from the library of heavy chains and a fragment derived from the library of light chains result in a viable phage.

For the creation of the libraries of heavy and light chains, preparations of messenger DNA isolated from cells from the organism or hybridomas may be used. The corresponding complementary DNA are then synthesized in a PCR amplification system. These techniques are well known to a person skilled in the art and are in particular described in "Molecular cloning; a Laboratory Manual" (Sambrok et al., 1989, previously referred to).

The selection of the bacteria expressing the complete molecules in step h) is followed by a step for selecting the clones synthesizing the required molecules.

The assembly of the parts of the heavy and light chains thus obtained can lead uniquely to the production of the Fab fragment. The vector is then modified so that it can code for the Fc fragment. The expression product of this vector is thus an antibody.

In order to select the antibody-synthesizing clones, the selection method described by Huse et al. (previously referred to) for the selection of clones synthesizing antibodies directed against paranitrophenyl phosphonamidate (NPN) may be used.

The method used in this article consists of making duplicates on nitrocellulose sheet of clones spread on dishes of gel culture medium and testing the hybridization of NPN coupled with $^{125}$I-labeled bovine serum albumin.

The present invention also relates to pharmaceutical compositions, drugs and diagnostic reagents containing products obtained by one of the methods of the present invention.

In particular, the products from expression in eukaryotic or prokaryotic cells transfected with recombinant plasmids including genes of rabbit or mouse origin may be used in human or veterinary diagnostic kits.

The present invention in addition relates to immunogenic compositions and antibodies obtained by one of the methods of the invention.

The present invention is illustrated without in any way being restricted by the following examples of its application in which:

FIG. 1 represents the sequences of junctions (SEQ ID NOS: 1–18) formed on the pBlueRec plasmid after co-transfection with p Rag-1 and p Rag-2 in NIH-3T3 fibroblasts.

FIG. 2 represents the sequences of junctions (SEQ ID NOS: 1, 19–51) formed on the pBlueRec plasmid after co-transfection with the vectors coding for Rag-1, Rag-2 and the TdT in NIH-3T3 fibroblasts.

FIG. 3 represents the sequences of junctions (SEQ ID NOS: 1, 52–62) formed on pBlueRec after co-transfection with the vectors coding for Rag-1 and Rag-2 in the cell lines BW1J, CHO-K1 and A.9.

In these three figures, the sequences of the recombined plasmids are aligned with the sequence of the original pBlueRec plasmid, which is shown at the top of each figure.

In these three figures, the nucleotides presumed to be due to type P insertions are underlined in the central parts of the figures, while the type N insertions shown in the same parts are not underlined. The deletions are represented by broken lines.

EXAMPLES

Materials and methods used in these examples

Cell line

The NIH-3T3 fibroblasts from mouse embryos (ATCC CRL 6442) and the A9 cells derived from L cells (ATCC CRL 6319) were cultivated in DMEM supplemented with 10% of calf foetus serum.

The BW1J mouse hepatoma cells were cultivated as described by Cassio D. and Weiss M. C. (Somat Cell Genet, 5, 719–738, 1979). The CHO-K1 Chinese hamster ovarian cells (ATCC CCL 61) were cultivated in RPMI supplemented with 10% of calf foetus serum.

The BASP-1 pre-B cells (Choquet et al., Science, 235, 1211–1214, 1987) were cultivated in RPMI supplemented with 10% of calf foetus serum and 50 pm of 9-mercaptoethanol.

Cloninc of the aene coding for the mouse terminal deoxvnucleotidvl transferase.

The RNA was prepared from the thymuses of five-week-old mice as described by Auffray and Rougeon (Europe J. Biochem., 107, 303–314, 980), but using 4M guanidine thiocyanate in place of the 6M urea.

The poly-A RNA was purified by use of oligo DT cellulose chromatography and analyzed by Northern blot. The synthesis of the single strand was carried out with 5 µg of poly-A RNA initiated with oligo DT using the MMLV inverse transcriptase (marketed by BRL).

The double strand synthesis was carried out in the presence of DNA polymerase I and RNase H.

The double-strand adapters with BstX1 terminals were linked to suitably prepared CDNA and cloned in the BstX1 restriction site of pCDNA2 (marketed by In Nitrogen).

The library of mouse thymus complementary DNA was screened with two mixed oligonucleotides corresponding respectively to the sequences 121–142 and 1471–1494 of the mouse TdT complementary DNA sequence.

The positive complementary DNA clones which were assumed to be sufficiently long to contain the whole of the gene coding for the mouse TdT were sequenced onto the two strands by the dideoxy termination method (Sanger et al., PNAS, 74, 5463–5467, 1977).

Vectors used.

The pBlueRec plasmid was as described by Kallenbach et al. [(1990) Nucleic Acid Research 18, 6730].

p Rag-1 and p Rag-2 were supplied by Qettinger et al. (previously referred to).

The complementary DNA from the mouse TdT was cloned in the pCDNA1. The expression of the Rag-1, Rag-2 and the TdT were under the control of the CMV promoter.

Demonstration of the specific recombination

The transfections were carried out by electroporation following the procedure described by Chu et al. (Nucleic Acid Research Res., 15, 1311–1326, 1987).

$2.10^6$ cells were transfected with 2.5 µg of pBlueRec with or without 6 µg of p Rag-1 or 4.8 µg of p Rag-2.

In order to determine the effect of the TdT on the N region insertion, 4.5 µg of the TdT expression vector were added to the three vectors previously mentioned.

The cells were collected after 40 to 48 hours incubation at 37° C., washed with PBS and the plasmid DNA was prepared according to Birnboim and Doly (Nucleic Acids Res. 7, 1513–1523, 1979).

The DNA sediments were resuspended in 20 µl of sterile water. 7 µl of the DNA solution were digested by Dpn1 in order to eliminate the plasmids which had not replicated. 40 µl of XL1-Blue competent bacteria (marketed by Stratagene) were transformed by electroporation and spread on LB Agar dishes containing XGal (80 µg/ml), IPTG (150 µM), ampicillin (100 µg/ml) and tetracycline (10 µg/ml).

The rearrangement frequency was calculated as the quantity of blue colonies×3 divided by the total number of clones.

Recombinant clone seauencina

The blue colonies were subcultured and isolated on LB Agar dishes containing XGal, IPTG, ampicillin and tetracycline.

The DNA preparations were carried out according to the method described by Sambrok et al. (Molecular cloning, Laboratory Manual previously referred to), then treated with RNase for two hours at room temperature before carrying out the double-strand sequencing.

Example 1

Comparison of the recombination frequencies in the NIH-3T3 fibroblasts and in the B cell precursor cell lines in the presence of Raa-1 and Raa-2.

The recombinant activity caused by Rag-1 and Rag-2 in the NIH-3T3 fibroblasts was tested by transient transfection.

p Rag-1 and p Rag-2 were co-transfected in the NIH3 fibroblasts with the pBlueRec plasmid recombination substrate.

After 48 hours, the plasmid DNA was isolated and tested in E. coli for recombination.

The LacZ sequence of pBlueRec was interrupted by a DNA fragment of 280 base pairs bordered by two RSS.

The site-specific rearrangement eliminated the insertion and in one out of three cases restored the correct-reading framework, giving rise to blue clones after transformation of E. Coli.

This rapid test enabled a substantial number of rearrangements to be examined.

The transfection experiments with p Rag-1 or p Rag-2 alone did not give rise to recombinant clones.

As shown in Table I, a significant recombination frequency was observed when the two plasmids were co-transfected. In addition the frequency (geometric mean= 1.26) was comparable with that observed after transfection of the recombination substrate in the pre B cells, BASP1 (geometric mean=1.46).

In order to compare the coding junctions formed after the recombination modulated in the fibroblasts by p Rag-1 and p Rag-2, with the junctions observed in the lymphoid cells, the junctions in the rearranged plasmids obtained after transfection of the NIH-3T3 cells were sequenced.

The sequences shown in FIG. 1 represent independent recombination data, i.e. the results of different transfection experiments.

Seven out of 17 junctions showed neither insertions nor deletions.

Four junctions had deletions on one side and four others had deletions on both sides.

Only one junction showed a type P insertion of two base pairs associated with a deletion of two base pairs on one side of the junction.

The last junction showed a deletion of one base pair and an addition of one nucleotide, which can be attributed to the heptamer and is probably due to an imprecise excision.

Example 2

Co-transfection with Rac-1 and Raa-2 and TdT of the NIH-3T3 fibroblasts.

In order to attempt to reconstitute the junctional diversity observed in the pre-B or pre-T cells, the NIH-3T3 fibroblasts were transfected with the expression vector of the TdT as well as with p R-1, p Rag-2 and pBlueRec.

The recombinant plasmids were sequenced.

Control transfections carried out with the pCDNA1 vector without the complementary DNA from the TdT did not lead to any insertion of N regions.

As shown in FIG. 2, 88% of the junctions revealed that there had been N region insertions. The majority of N regions were from 1 to 4 nucleotides with an average of 3 nucleotides per junction.

Nevertheless an unusual insertion of 18 nucleotides was observed.

The TdT incorporated the G residues more efficiently than the other nucleotides. The frequency of type P nucleotide insertion seemed to have increased in this experiment. It should however be noted that it is impossible to distinguish them from the N regions.

Example 3

Effect of Rag-1 and Rag-2 in different types of differentiated cell lines.

In the preceding examples it has been shown that Rag-1 and Rag-2 are capable of causing a recombination activity in the relatively undifferentiated cells NIH-3T3 fibroblasts.

The activity of these two genes was thus tested in cells in differentiated states. The results obtained in the BW1J, CHO-K1 and A9 cell lines are shown in table 2.

Variations between the different cell lines can be seen, but surprisingly the rearrangement frequencies in the BWLJ and CHO-K1 lines were clearly higher than those obtained for the 3T3 fibroblasts.

The rearrangements could be detected 13 hours after transfection with pBlueRec, p Rag-1 and p Rag-2.

The sequencing of the recombined plasmids showed that deletions at the coding junctions had taken place in the three cell lines tested (FIG. 3).

A single type P nucleotide insertion was found at the junction of a recombinant clone obtained after transfection of the A9 lines.

CONCLUSIONS

The results overall show that nucleotide deletions are obtained in undifferentiated lines after co-transfection with p R-1 and p Rag-2. In addition type P nucleotide insertions such as those defined by Lafaille et al. (Cell, 59, 859–870, 1989) were observed.

It was moreover observed that the co-expression of Rag-1, Rag-2 and TdT in the undifferentiated cells leads to type N insertions.

These results thus show that Rag-1 and Rag-2 are sufficient to induce a site-specific recombination but that the presence of the TdT, in combination with R-1 and Rag-2, is necessary for obtaining type N insertions which are a reflection of the expression of the diversity of the synthesis of the immunoglobulins and the lymphoid cell receptors.

TABLE I

Rearrangements in the fibroblasts and the B cell precursors

| Cell line | DNA | Amp$^R$ colonies Total | Blue | R = 3 × Blue × 10$^{-2}$ Total |
|---|---|---|---|---|
| NIH-3T3 | pBlueRec | 70,000 | 0 | 0 |
| | pBlueRec, pRag1 | 34,860 | 0 | 0 |
| | pBlueRec, pRag2 | 12,140 | 0 | 0 |
| | pBlueRec, pRag1, pRag2 | 144,000 | 183 | 0.38 |
| | pBlueRec, pRag1, pRag2 | 38,000 | 128 | 1 |
| | pBlueRec, pRag1, pRag2 | 60,000 | 1059 | 5.3 |
| BASP-1 | pBlueRec | 14,400 | 186 | 1.3 |
| | pBlueRec | 14,800 | 237 | 1.6 |
| | pBlueRec | 12,960 | 190 | 1.5 |

R = recombination frequency

TABLE II

Frequency of rearrangements in three cell lines

| Cell line | DNA | Amp$^R$ colonies Total | Blue | R = 3 × Blue × 10$^{-2}$ Total |
|---|---|---|---|---|
| A9 | pBlueRec, pRag1, pRag2 | 16,800 | 0 | 0 |
| | pBlueRec, pRag1, pRag2 | 5,620 | 71 | 3.8 |
| BW1J | pBlueRec | 12,000 | 0 | 0 |
| | pBlueRec, pRag1, pRag2 | 5,600 | 83 | 4.4 |
| | pBlueRec, pRag1, pRag2 | 1,800 | 8 | 1.3 |
| | pBlueRec | 16,000 | 1050 | 19.6 |
| CHO-K1 | pBlueRec | 3,434 | 0 | 0 |
| | pBlueRec, pRag1, pRag2 | 2,300 | 38 | 4.9 |
| | pBlueRec, pRag1, pRag2 | 1,996 | 149 | 22.3 |

R = recombination frequency

We claim:

1. An isolated nucleic acid comprising nucleotide sequences including the Rag-1 and Rag-2 genes and the gene which codes for terminal deoxymucleotidyl transferase (TdT).

2. The isolated nucleic acid according to claim 1, wherein the nucleotide sequences are included in vectors.

3. A composition comprising the plasmids pBluerec, pRag-1, pRag-2, and pMTdT.

4. A composition comprising a combination of synergistic quantities of the products of expression of the Rag-1 and Rag-2 genes and a terminal deoxynucleotide transferase.

5. A method for generating structural diversity in a peptide sequence by randomly deleting or inserting nucleotides in a nucleotide sequence which codes for the peptide sequence, said method comprising the transfection of a mammalian cell preparation with one or more vectors expressing the products of the Rag-1 gene, Rag-2 gene and the terminal deoxynucleotidyl transferase (TdT) gene and by an identical or different vector including said nucleotide sequence bordered by one or more recombination signal sequences (RSS) to produce a recombined vector or vectors that express said nucleotide sequence to produce a mutated peptide.

6. A method for generating structural diversity in a peptide sequence by randomly deleting or inserting nucleotides in a nucleotide sequence which codes for the peptide sequence, the method comprising the transfection of a mammalian cell preparation with a vector including the nucleotide sequence bordered by one or more RSS recombination sequences, then in a second step transfection by one or more identical or different vectors expressing the products of the Rag-1 gene, Rag-2 gene and terminal deoxynucleotidyl transferase gene to produce a recombined vector or vectors that express said nucleotide sequence to produce a mutated peptide.

7. A method for generating structural diversity in a peptide sequence by introducing into a nucleotide sequence corresponding to the peptide sequence insertions or deletions resulting from the inverse repetition of sequences adjacent to one or more RSS recombination sequences, said method comprising the transfection of a mammalian cell preparation with one or more vectors expressing the products of the Rag-1 and Rag-2 genes and by an identical or different vector including the nucleotide sequence bordered by one or more RSS sequences to produce a recombined vector or vectors that express said nucleic sequence to produce a mutated peptide.

8. A method for generating structural diversity in a peptide sequence by introducing into a nucleotide sequence corresponding to the peptide sequence insertions or deletions resulting from the inverse repetition of sequences adjacent to one or more RSS recombination sequences, said method comprising the transfection of a mammalian cell preparation with a vector including the nucleotide sequence bordered by one or more RSS sequences or by one, then in a second step transfection by one or more identical or different vectors expressing the products of the Rag-1 and Rag-2 genes to produce a recombined vector or vectors that express said nucleotide sequence to produce a mutated peptide.

9. The method according to one of claims 5 to 8, wherein the recombined vector or vectors including a nucleotide sequence corresponding to the peptide sequence are transferred into bacteria in order to select proteins showing a required structure.

10. The method according to one of claims 5 to 8, for obtaining structurally diverse immunoglobulins by separate rearrangement of genes encoding light and heavy chains and co-expression of the two chains.

11. The method according to one of claims 5 to 8, for obtaining structurally diverse receptors of lymphoid cells by rearrangement of genes encoding the alpha, beta, gamma and/or delta chains of the T cell receptors.

12. The method according to claim 10, wherein the rearrangement of genes encoding the light chains is carried out in the presence of the nucleotide sequences of the Rag-1 and Rag-2 genes.

13. The method according to claim 10, wherein the rearrangement of genes encoding the heavy chains is carried out in the presence of nucleotide sequences of the Rag-1 and Rag-2 genes and the gene for the terminal deoxynucleotidyl transferase.

14. The method according to one of claims 5 to 8, comprising the steps of:

a) transfection of a mammalian cell preparation with one or more vectors including a nucleotide sequence which codes for the peptide sequence for which the variability is desired and by one or more identical or different vectors expressing the Rag-1 and Rag-2 genes or expressing the Rag-1, Rag-2 and the TdT genes;

b) isolation of the DNA of the vectors of the cell preparations;

c) removal of the vectors which have not undergone recombination;

d) transformation of the cell hosts by the vectors resulting from step c), and e) selection of the cells expressing the molecules showing a desired structure.

15. The method according to claim 14, wherein the said peptide sequence is an alpha, beta, gamma or delta chain of the lymphoid cell receptors.

16. The method according to claim 10, comprising the steps of:

a) co-transfection of a mammalian cell preparation with one or more vectors including non-rearranged nucleotide sequences which code for light chains and by one or more vectors expressing the Rag-1 and Rag-2 genes, and b) co-transfection of another cell preparation by one or more vectors including the non-rearranged nucleotide sequences which code for heavy chains and by one or more vectors expressing the gene for the terminal deoxynucleotidyl transferase as well as the Rag-1 and Rag-2 genes, c) isolation of the vector DNA of the two cell preparations, d) removal of the vectors which have not undergone recombination, e) transformation of at least two bacterial cultures, each by one of the two isolated vector DNAs obtained from the two cell preparations obtained from step d), f) amplification and preparation of the vector DNA, g) insertion of the genes which code for the heavy and light chains into the same vector, h) transformation of cells by the vector obtained from step f), and i) selection of cells expressing the complete immunoglobulin molecules.

17. The method according to claim 16, wherein the vectors obtained at step c) that have not undergone recombination are removed by enzymatic digestion.

18. The method according to claim 16, wherein the preparations are fibroblasts or any other mammalian cells.

19. Plasmid pMTdT including the gene for the terminal deoxyribonucleotidyl transferase deposited with the Microorganism Culture National Collection under the N. I 1160.

20. The method according to claim 16, wherein the vector expressing the terminal deoxyribonucleotidyl transferase is the plasmid pMTdT deposited with the Microorganism Culture National Collection under the No. I 1160.

* * * * *

SEQUENCE LISTING ( 1 ) GENERAL INFORMATION:

( i i i ) NUMBER OF SEQUENCES: 62

( 2 ) INFORMATION FOR SEQ ID NO:1:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

CCGCTCTAGA ACTAGTGGAT CCCACAGTGC ACTGTGGTCG ACCTCGAGGG G        51

( 2 ) INFORMATION FOR SEQ ID NO:2:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:2:

CCGCTCTAGA ACTAGTGGAT ACCTCGAGGG G        31

( 2 ) INFORMATION FOR SEQ ID NO:3:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

CCGCTCTAGA ACTAGTGGAT CCGTCGACCT CGAGGGG        37

( 2 ) INFORMATION FOR SEQ ID NO:4:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:4:

CCGCTCTAGA ACTAGTGGAT CCGTCGACCT CGAGGGG        37

( 2 ) INFORMATION FOR SEQ ID NO:5:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

CCGCTCTAGA ACTAGTGGAT CCGTCGACCT CGAGGGG   37

( 2 ) INFORMATION FOR SEQ ID NO:6:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CCGCTCTAGA ACTAGTGGAT CCGTCGACCT CGAGGGG   37

( 2 ) INFORMATION FOR SEQ ID NO:7:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CCGCTCTAGA ACTAGTGGAT CCGACCTCGA GGGG   34

( 2 ) INFORMATION FOR SEQ ID NO:8:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCGCTCTAGA ACTAGTGGAT CCGTCGACCT CGAGGGG   37

( 2 ) INFORMATION FOR SEQ ID NO:9:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CCGCTCTAGA ACTAGTGGAT CCGACCTCGA GGGG   34

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CCGCTCTAGA ACTAGTGGCG ACCTCGAGGG G   31

( 2 ) INFORMATION FOR SEQ ID NO:11:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

CCGCTCTAGA ACTAGTGGAT CCGACCTCGA GGGG      34

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CCGCTCTAGA ACTAGTGTCG AGGGG      25

( 2 ) INFORMATION FOR SEQ ID NO:13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CCGCTCTAGA ACTAGTGGAT CCGTCGACCT CGAGGGG      37

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CCGCTCTAGA ACTAGTGGAT CCGACCTCGA GGGG      34

( 2 ) INFORMATION FOR SEQ ID NO:15:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CCGCTCTAGA ACTAGTGGAT CCGTCGACCT CGAGGGG      37

( 2 ) INFORMATION FOR SEQ ID NO:16:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CCGCTCTAGA ACTAGTGGAT CCGGCGACCT CGAGGGG    37

( 2 ) INFORMATION FOR SEQ ID NO:17:

( i ) SEQUENCE CHARACTERISTICS:
       ( A ) LENGTH: 31 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:17:

CCGCTCTAGA ACTAGTGGCG ACCTCGAGGG G    31

( 2 ) INFORMATION FOR SEQ ID NO:18:

( i ) SEQUENCE CHARACTERISTICS:
       ( A ) LENGTH: 37 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:18:

CCGCTCTAGA ACTAGTGGAT CCCTCGACCT CGAGGGG    37

( 2 ) INFORMATION FOR SEQ ID NO:19:

( i ) SEQUENCE CHARACTERISTICS:
       ( A ) LENGTH: 37 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:19:

CCGCTCTAGA ACTAGTGGGT TCGTCGACCT CGAGGGG    37

( 2 ) INFORMATION FOR SEQ ID NO:20:

( i ) SEQUENCE CHARACTERISTICS:
       ( A ) LENGTH: 34 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:20:

CCGCTCTAGA ACTAGTGGAT CCGGCCTCGA GGGG    34

( 2 ) INFORMATION FOR SEQ ID NO:21:

( i ) SEQUENCE CHARACTERISTICS:
       ( A ) LENGTH: 37 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:21:

```
CCGCTCTAGA ACTAGTGGGG CCGTCGACCT CGAGGGG                                         37
```

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
CCGCTCTTTC GTCGACCTCG AGGGG                                                      25
```

( 2 ) INFORMATION FOR SEQ ID NO:23:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
CCGCTCTAGA ACTAGTTTCC TCGAGGGG                                                   28
```

( 2 ) INFORMATION FOR SEQ ID NO:24:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
CCGCTCTAGA ACTAGTGGGG TCGACCTCGA GGGG                                            34
```

( 2 ) INFORMATION FOR SEQ ID NO:25:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

```
CCGCTCTAGA ACTAGTGGAT CCCCAGACCT CGAGGGG                                         37
```

( 2 ) INFORMATION FOR SEQ ID NO:26:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
CCGCTCTAGA ACTTTCGACC TCGAGGGG                                                   28
```

( 2 ) INFORMATION FOR SEQ ID NO:27:

( i ) SEQUENCE CHARACTERISTICS:
   ( A ) LENGTH: 40 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:27:

CCGCTCTAGA ACTAGTGGAT CCGACGTCGA CCTCGAGGGG          40

( 2 ) INFORMATION FOR SEQ ID NO:28:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:28:

CCGCTCTAGA ACTAGTGGAT CCATCCGACC TCAGGGG          37

( 2 ) INFORMATION FOR SEQ ID NO:29:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:29:

CCGCTCTAGA ACTAGTGGAT CCAACCTCGA GGGG          34

( 2 ) INFORMATION FOR SEQ ID NO:30:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:30:

CCGCTCTAGA ACTAGTGACC TCGAGGGG          28

( 2 ) INFORMATION FOR SEQ ID NO:31:

( i ) SEQUENCE CHARACTERISTICS:
      ( A ) LENGTH: 40 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:31:

CCGCTCTAGA ACTAGTGGAT CCTCCGTCGA CCTCGAGGGG          40

( 2 ) INFORMATION FOR SEQ ID NO:32:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear (i i) MOLECULE TYPE: DNA (genomic)

(x i) SEQUENCE DESCRIPTION: SEQ ID NO:32:

CCGCTCTAGA ACTAGTGGAT CCGTCGACCT CGAGGGG 37

(2) INFORMATION FOR SEQ ID NO:33:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:33:

CCGCTCTAGA ACTAGTGGAT CCCTCGTCGA CCTCGAGGGG 40

(2) INFORMATION FOR SEQ ID NO:34:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:34:

CCGCTCTAGA ACTAGTGGGT CCGTCGACCT CGAGGGG 37

(2) INFORMATION FOR SEQ ID NO:35:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:35:

CCGCTCTAGA ACTAGTGGAT CGGGCCTCGA GGGG 34

(2) INFORMATION FOR SEQ ID NO:36:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:36:

CCGCTCTAGA ACTAGTGGAT CCGAGGTCGA CCTCGAGGGG 40

(2) INFORMATION FOR SEQ ID NO:37:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:37:

CCGCTCTAGA ACTAGTGGAT CGGACCTCGA GGGG        34

( 2 ) INFORMATION FOR SEQ ID NO:38:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

CCGCTCTAGA ACTAGTGGAT CCGTCGACCT CGAGGGG        37

( 2 ) INFORMATION FOR SEQ ID NO:39:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

CCGCTCTAGA ACTAGTGGAT ACCATACCCC TTTACCAATC GACCTCGAGG GG        52

( 2 ) INFORMATION FOR SEQ ID NO:40:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

CCGCTCGAGA ACTAGTGGAT CCCCCCCGC CGTCGACCTC GAGGGG        46

( 2 ) INFORMATION FOR SEQ ID NO:41:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

CCGCTCTAGA ACTAGTGGTC CTCCTCGAGG GG        32

( 2 ) INFORMATION FOR SEQ ID NO:42:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

CCGCTCTAGA ACTAGTGGAT CACACCTCGA GGGG        34

( 2 ) INFORMATION FOR SEQ ID NO:43:

( i ) SEQUENCE CHARACTERISTICS:
   ( A ) LENGTH: 32 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:43:

CCGCTCTAGA ACTAGTGGCC GACCTCGAGG GG                            32

( 2 ) INFORMATION FOR SEQ ID NO:44:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:44:

CCGCTCTAGA ACTAGCCCTA CCGACCTCGA GGGG                          34

( 2 ) INFORMATION FOR SEQ ID NO:45:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:45:

CCGCTCTAGA ACTAGTGGCC CCGACCTCGA GGGG                          34

( 2 ) INFORMATION FOR SEQ ID NO:46:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:46:

CCGCTCTAGA ACTAGTGGAT CCGTCGACCT CGAGGGG                       37

( 2 ) INFORMATION FOR SEQ ID NO:47:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:47:

CCGCTCTAGA ACTAGTGGTC CCGACCTCGA GGGG                          34

( 2 ) INFORMATION FOR SEQ ID NO:48:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear (i i) MOLECULE TYPE: DNA (genomic)

(x i) SEQUENCE DESCRIPTION: SEQ ID NO:48:

CCGCTCTAGA ACTAGTGGAT TCGTCGACCT CGAGGGG   37

(2) INFORMATION FOR SEQ ID NO:49:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:49:

CCGCTCTAGA ACTAGTGGTC TCGACCTCGA GGGG   34

(2) INFORMATION FOR SEQ ID NO:50:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:50:

CCGCTCTAGA ACTAGTGGAT CCAACCTCGA GGGG   34

(2) INFORMATION FOR SEQ ID NO:51:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:51:

CCGCTCTAGA ACTAGTGGAT CCCCCGTCGA CCTCGAGGGG   40

(2) INFORMATION FOR SEQ ID NO:52:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:52:

CCGCTCTAGA ACTAGTGGGA CCTCGAGGGG   30

(2) INFORMATION FOR SEQ ID NO:53:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:53:

CCGCTCTAGA ACTAGTGGAC CTCGAGGGG                    29

( 2 ) INFORMATION FOR SEQ ID NO:54:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

CCGCTCTAGA ACTAGTGGAT CCGTCGACCT CGAGGGG           37

( 2 ) INFORMATION FOR SEQ ID NO:55:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

CCGCTCTAGA ACTAGTGGAT CCGACCTCGA GGGG              34

( 2 ) INFORMATION FOR SEQ ID NO:56:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

CCGCTCTAGA ACTAGTGGAT CCGACCTCGA GGGG              34

( 2 ) INFORMATION FOR SEQ ID NO:57:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

CCGCTCTAGA ACTAGTGGAT CCGTCGACCT CGAGGGG           37

( 2 ) INFORMATION FOR SEQ ID NO:58:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

CCGCTCTAGA ACTAGTGGAT CCGGCCTCGA GGGG              34

( 2 ) INFORMATION FOR SEQ ID NO:59:

(i) SEQUENCE CHARACTERISTICS:
  (A) LENGTH: 37 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:59:

CCGCTCTAGA ACTAGTGGAT CCGTCGACCT CGAGGGG    37

(2) INFORMATION FOR SEQ ID NO:60:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:60:

CCGCGACCTC GAGGGG    16

(2) INFORMATION FOR SEQ ID NO:61:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:61:

CCGCGTCGAC CTCGAGGGG    19

(2) INFORMATION FOR SEQ ID NO:62:

(i) SEQUENCE CHARACTERISTICS:
  (A) LENGTH: 33 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:62:

CCGCTCTAGA ACTAGTGGAT CGACCTCGAG GGG    33